US008951724B2

(12) United States Patent
Gleicher et al.

(10) Patent No.: US 8,951,724 B2
(45) Date of Patent: *Feb. 10, 2015

(54) DETECTION OF INFERTILITY RISK AND PREMATURE OVARIAN AGING

(71) Applicants: Norbert Gleicher, New York City, NY (US); David H Barad, Closter, NJ (US)

(72) Inventors: Norbert Gleicher, New York City, NY (US); David H Barad, Closter, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/220,919

(22) Filed: Mar. 20, 2014

(65) Prior Publication Data

US 2014/0206756 A1    Jul. 24, 2014

Related U.S. Application Data

(60) Continuation-in-part of application No. 14/101,646, filed on Dec. 10, 2013, which is a division of application No. 13/612,566, filed on Sep. 12, 2012, now Pat. No. 8,629,120, which is a continuation-in-part of application No. 13/360,349, filed on Jan. 27, 2012, now abandoned, which is a continuation-in-part of application No. 13/043,199, filed on Mar. 8, 2011, which is a continuation-in-part of application No. 12/508,295, filed on Jul. 23, 2009, now abandoned.

(51) Int. Cl.
*C12Q 1/68* (2006.01)
*A61K 48/00* (2006.01)
*C07H 21/02* (2006.01)
*C07H 21/04* (2006.01)

(52) U.S. Cl.
USPC ................................ 435/6; 514/44; 536/23.1

(58) Field of Classification Search
None
See application file for complete search history.

(56) References Cited

PUBLICATIONS

Bagni C, Tassone F, Neri G, Hagerman R. Fragile X syndrome: causes, diagnosis, mechanisms, and therapeutics. J Clin Invest. 2012;122:4314-22.
Willemsen R, Levenga J, Oostra BA. CGG repeat in the FMR1 gene: size matters. Clin Genet. 2011;80:214-25.
Hoffman GE, et al.Ovarian abnormalities in a mouse model of fragile X primary ovarian insufficiency. J. Histochem Cytochem. 2012; 60:439-56.
Gleicher N, Weghofer A, Barad DH. Effects of race/ethnicity on triple CGG counts in the FMR1 gene in infertile women and egg donors. Reprod Biomed Online. 2010;20:485-91.
Nelson LM. Clinical practice. Primary ovarian insufficiency. N Engl J Med. 2009;360:606-14.
Baker VL. Primary ovarian insufficiency in the adolescent. Curr Opin Obstet Gynecol. 2013;25:375-81.

Gleicher N, et al. Intermediate and normal sized CGG repeat on the FMR1 gene does not negatively affect donor ovarian response. Hum Reprod. 2012;27:2241-2; author reply 2-3.
Lledo B, Guerrero J, et al. Intermediate and normal sized CGG repeat on the FMR1 gene does not negatively affect donor ovarian response. Hum Reprod. 2012;27:609-14.
Nelson SM. Biomarkers of ovarian response: current and future applications. Fertil Steril. 2013;99:963-9.
Ferder I, et al. Expression of fragile X mental retardation protein and Fmr1 mRNA during folliculogenesis in the rat. Reproduction 2013;145:335-43.
Gleicher N, et al. Hypoandrogenism in association with diminished functional ovarian reserve. Hum Reprod. 2013;28:1084-91.
Donnez J. Introduction: fertility preservation, from cancer to benign disease to social reasons: the challenge of the present decade. Fertil Steril. 2013;99:1467-8.
Waimev KE, et al. Future directions in oncofertility and fertility preservation: A report from the 2011 Oncofertility Consortium Conference. J Adolesc Young Adult Oncol 2013.
Donnez J. Introduction: Fertility preservation, from cancer to benign disease to social reasons: the challenge of the present decade. Fertil Steril 2013;99:1467-1468.
Cobo A, et al. is vitrification of oocytes useful for fertility preservation for age-related fertility decline and in cancer patients? Fertil Steril 2013; 99:1485-1495.
Bedoschi G, Turan V, Oktay K. Fertility preservation options in women with endometriosis. Minerva Gynecol2013;65:99-103.
Gleicher N, Weghofer A, Barad DH. Defining ovarian reserve to better understand ovarian aging. Reprod Bioi Endocrinol 2011;9:23.
Cil AP, et al.Age-specific probability of live birth with oocyte preservation:an individual patient data meta-analysis. Fertile Steril 2013;doi:10.1016/j.fertnstert.2013.04.023.
Dunlop CE, et al. Ovarian stem cells—Potential roles in infertility treatment and fertility preservation. Maturitas 2013; doi: 10.1016/j.maturitas Apr. 1, 2013.
Voorhuis M, Broekmans FJ, Fauser BC, Onland-Moret NC, van der Schouw YT. J Clin Endocrinol Metab 2011;96: E473-479.
Ledger WL. Clinical utility of measurement of anti-mullerian hormone in reproductive endocrinology. 1 Clin Endocrinol Metab 2010;95:5144-5154.

(Continued)

*Primary Examiner* — Amy Bowman
(74) *Attorney, Agent, or Firm* — Davidoff Hutcher & Citron LLP; Michael A. Adler

(57) ABSTRACT

Method of early detection of risk of infertility and ovarian aging in and treatment of a human female who has not experienced infertility and is not otherwise indicated to have premature ovarian aging. A number of CGG repeats on each allele of the isolated FMR1 gene is measured by using an assay, and a testing regimen is performed only when the determined number of CGG repeats on one of the FMR1 gene alleles is less than 26. The testing regimen includes periodically measuring serum level of a hormone related to fertility, such as Anti-Müllerian Hormone, Follicle Stimulating Hormone and/or estradiol over a period of about three to eight years and, after each measurement, determining if the measured serum level is less than a set confidence interval for a human female of the same age of the female. If so, the human female is treated for premature ovarian aging.

15 Claims, 11 Drawing Sheets

(56) References Cited

PUBLICATIONS

Kushnir VA, Yu Y, Himaya E, Barad DH, Weghofer A, Lee H-J, Wu Y-G, Shohat-Tal A, Lazzaroni-Tealdi E, Gleicher N FMR1 Gene Mutations Already at Young Ages Are Predictive of Later Premature Ovarian Senescence and Infertility, 2014.

Michels AW, Gottlieb PA. Autimmune polyglandular syndromes. Nat Rev Endocrinol 2010;6:270-277.

Gleicher N, et al. The impact in older women of ovarian FMR1 genotypes and sub-genotypes on ovarian reserve. PLoS One 2012;7:e33638.

Nelson SM, et al. AntiMullerian hormone: clairvoyance or crystal clear? Hum Reprod 2012;27:631-636.

Fleming R, Nelson SM. Reproducibility of AMH. Hum Reprod 2012;27:3639-3641.

Kelsey TW, et al. A validated model of serum anti-Mi.illerian hormone from conception to menopause. Plos One 2011;6: e22024.

Bianchi I, Ileo A, Gershwin ME, Invernizzi P. The X chromosome and immune associated genes. J Autoimmun 2012;38:J187-192.

Bukalov VK, et al. Autoimmune disorders in women with turner syndrome and women with karyotypically normal primary ovarian insufficiency. J Autoimmun 2012;38:315-322.

Ueo A, Moroni I, Caliari I, Invernizzi P. Autoimmunity and Turner's syndrome. Autoimmune Rev 2012;11:A538-543.

Cushman RA. Evidence that the autoimmune regulator gene influences thymic production of ovarian antigens and prevents autoimmune-mediated premature reproductive senescence. Biology of Reproduction, Jan. 2012, 109.

van Asselt KM, Kok HS, Pearson PI, Dubas JS, Peeters PH, Te Velde ER, van Noord PA, Heritability of menopausal age in mothers and daughters. Fertil Steril 2004;82:1348-1351.

Gleicher N, Kushnir VA, Barad DH, Can We Develop a New Paradigm in Adolescent and Young Adult Gynecology by Prospectively Assessing Risk for Premature Ovarian Senescence?, 2014.

Morris DH, et al. Familial concordance for age at natural menopause; results from he Breakthrough generations Study. Menopause 2011;18:956-961.

Weghofer A, Kim A, Barad DH, Gleicher N. Age at menarche: a predictor of diminished ovarian function. Feril Steril2013;100:1039-1043.

Anderson RA, Nelson SM, Wallace WH. Measuring anti-Mullerian hormone for the assessment of ovarian reserve: when and for whom is it indicated? Maturitas 2012;71:28-33.

Kallio S, et al. Antimullerian hormone levels decrease in women using combined contraception independently of administered route. Fertil Steril 2013;99:1305-1310.

Robertson DM, et al. Changes in serum antimullerian hormone levels across the ovulatory menstrual cycle in late reproductive age. Menopause 2011;18:521-524.

Hadlow N, et al. Variation in antimullerian hormone concentration during menstrual cycle may change the clinical classification of the ovarian response. Fertil Steril2013;99:17.

Sen A, Kushnir VA, Barad DH, Gleicher N. Endocrine autoimmune diseases and female infertility. Nature Rev Endocrinol; 2013; In press.

Lamar C, et al. Ovarian reserve: Regulation and implications for women's health. Proceedings ofthe 2012 NICHD-ASRM Conference. J Assit Reprod Genet 2013;30:285-292.

| | Donors | Infertility Patients | P |
|---|---|---|---|
| Number | 233 | 354 | |
| Age (years) | 24.4±3.3 | 33.5±3.5 | <.0001 |
| AMH (ng/ml) | 4.3±2.6 | 1.9±2.1 | <.0001 |
| FSH (mIU/ml) | N/A | 13.2±17.3 | |
| BMI | 21.4±2.4 | 24.4±5.5 | <.0001 |
| FMR1 n (%) | | | |
| norm | 127 (54.5) | 209 (59.0) | |
| het-norm/ low | 50 (21.5) | 66 (18.6) | |
| het-norm/ high | 29 (12.5) | 62 (17.5) | 0.005 |
| hom-low/ low | 8 (3.4) | 10 (2.8) | |
| hom-high/ high | 10 (4.3) | 2 (0.6) | |
| hom-low/high | 9 (3.9) | 5 (1.4) | |

FIG. 6

| Parameter | | Estimate | Standard Error | t value | Pr > \|t\| |
|---|---|---|---|---|---|
| Intercept | | 1.7669 | 0.3012 | 5.87 | <.0001 |
| FMR1 | het-norm/high | 0.0716 | 0.1275 | 0.56 | 0.5747 |
| FMR1 | het-norm/low | -0.0030 | 0.1011 | -0.03 | 0.9766 |
| FMR1 | hom-high/high | -0.2526 | 0.1984 | -1.27 | 0.2043 |
| FMR1 | hom-low/high | -0.1699 | 0.2100 | -0.81 | 0.4192 |
| FMR1 | hom-low/low | -0.7202 | 0.2202 | -3.27 | 0.0012 |
| FMR1 | norm | 0.0000 | . | . | . |
| Age | | -0.0190 | 0.0124 | -1.53 | 0.1277 |

FIG. 7

| Parameter | | Estimate | Standard Error | Z | Pr > \|Z\| |
|---|---|---|---|---|---|
| Intercept | | 2.1464 | 0.2797 | 7.67 | <.0001 |
| FMR1 | het-norm/high | 0.1240 | 0.1134 | 1.09 | 0.2744 |
| FMR1 | het-norm/low | -0.0053 | 0.0990 | -0.05 | 0.9575 |
| FMR1 | hom-high/high | -0.4046 | 0.1146 | -3.53 | 0.0004 |
| FMR1 | hom-low/high | -0.2722 | 0.3407 | -0.80 | 0.4244 |
| FMR1 | hom-low/low | -0.8938 | 0.3258 | -2.74 | 0.0061 |
| Age | | -0.0349 | 0.0113 | -3.08 | 0.0020 |

FIG. 8

| Effect | FMR1 | Estimate | Standard Error | t Value | Pr > \|t\| |
|---|---|---|---|---|---|
| Intercept | | 2.2358 | 0.4514 | 4.95 | <.0001 |
| Time | | -0.0908 | 0.0294 | -3.09 | 0.0030 |
| *FMR1* | low | -0.0912 | 0.0896 | -1.02 | 0.3129 |
| *FMR1* | norm and high | 0 | . | . | . |
| Time**FMR1* | low | -0.1338 | 0.0657 | -2.04 | 0.0463 |
| Time**FMR1* | norm or high | 0 | . | . | . |
| Age(baseline) | | -0.0119 | 0.0123 | -0.96 | 0.3403 |
| BMI | | -0.0307 | 0.0170 | -1.80 | 0.0768 |

| Δ | $\bar{X} \pm SD$ |
|---|---|
| Δ norm | 1.39 (±1.28) |
| Δ het-norm/low | 1.75 (±1.31) |
| Δ het-norm/high | 1.29 (±1.13) |
| Δ hom-low/low | 0.87 (±0.74) |
| Δ hom-high/high | 1.13 (±1.32) |
| Δ hom-low/high | 2.17 (±0.87) |

FIG. 13

| Comparison | P-values |
|---|---|
| het-norm/low vs. norm | 0.0452 |
| het-norm/low vs. het-norm/high | 0.0416 |
| het-norm/low vs. hom | 0.1779 |
| het-norm/high vs. norm | 0.5907 |
| het-norm/high vs. hom | 0.9839 |
| norm vs. hom | 0.7412 |

DETECTION OF INFERTILITY RISK AND PREMATURE OVARIAN AGING

CROSS REFERENCE TO RELATED APPLICATIONS

This application is a continuation-in-part of U.S. patent application Ser. No. 14/101,646, filed on Dec. 10, 2013, which is a divisional of U.S. patent application Ser. No. 13/612,566, filed on Sep. 12, 2012, now U.S. Pat. No. 8,629,120, which is a continuation-in-part of U.S. patent application Ser. No. 13/360,349, filed on Jan. 27, 2012, which is a continuation-in-part of U.S. patent application Ser. No. 13/043,199, filed on Mar. 8, 2011, and of U.S. patent application Ser. No. 12/508,295, filed on Jul. 23, 2009, all of which are incorporated by reference herein.

BACKGROUND

1. Field of the Invention

The present invention relates generally to methods for assessing human female ovarian health by evaluating CGG repeats on the fragile X mental retardation 1 (FMR1) gene, and providing testing and treatment based on the evaluation. Particularly, the present invention provides methods for early detection of risk of infertility and/or imminent premature ovarian aging in a human female who has not experienced infertility and is not otherwise indicated to have premature ovarian aging. The present invention also provides methods for treatment of imminent premature ovarian aging in a human female, predicting infertility and determining the imminence of premature ovarian aging by analyzing the FMR1 gene and then performing a treatment and/or testing regimen depending on the results of the analysis. No prior known tests can detect imminent ovarian aging or infertility in a human female who has not experienced infertility and is not otherwise indicated to have premature ovarian aging.

2. Description of the Related Art

The following acronyms are used throughout this specification:

AIRE: Autoimmune Regulator
CGG: Cytosine-Guanine-Guanine
FMR1: Fragile X Mental Retardation 1
FMRP: Fragile X Mental Retardation Protein
FOR: Functional Ovarian Reserve
FXS: Fragile X Syndrome
OPOI: Occult Primary Ovarian Insufficiency
OR: Ovarian Reserve
POA: Premature Ovarian Aging
POF: Premature Ovarian Failure
POI: Primary Ovarian Insufficiency
POS: Premature Ovarian Senescence
TOR: Total Ovarian Reserve These acronyms also appear after the first use of each full term.

The FMR1 gene (gene location Xq27.3) is commonly studied or analyzed because of its association with Fragile X syndrome (FXS). FXS is the most common cause of familial mental retardation and autism (see, Bagni C., Tassone F., Neri G., Hagerman R., *Fragile X Syndrome: Causes, Diagnosis, Mechanisms, and Therapeutics*, The Journal of Clinical Investigation, December 2012, 4314-22, hereinafter referred to as "Bagni"). FXS occurs when the FMR1 gene is inactivated and does not produce Fragile X Mental Retardation Protein (FMRP). FMRP is important for proper neurological development and is involved in RNA translation. This inactivation is usually caused by too many Cytosine-Guanine-Guanine (CGG) trinucleotide repeats on the FMR1 gene. FMR1 genes are usually classified by the number of such CGG repeats on the gene. The usual classification in current medical practice recognizes four ranges of CGG repeats on the FMR1 gene: a normal (or common) range of $CGG_{n<45}$, an intermediate range of $CGG_{n\sim45\text{-}54}$, a premutation range of $CGG_{n\sim55\text{-}200}$ and a full mutation range of $CGG_{n>200}$. FXS usually occurs in persons with an FMR1 gene in the full mutation range. A gene in the premutation range can expand to the full mutation range in the next generation of offspring (see, Willemsen R., Levenga J., Oostra B. A., *CGG Repeat in the FMR1 Gene: Size Matters*, Clinical Genetics, September 2011; 214-25, hereinafter referred to as "Willemsen"). Because of such expansion, FXS risk screening focuses on women with FMR1 genes in the premutation range, who are at risk for having children with FXS. FXS risk screening is the primary purpose of FMR1 testing in current medical practice.

Y. H. Fu found a peak in the population distribution of CGG repeats in the range $CGG_{n=29\text{-}30}$ (see, Fu Y. H., Kuhl D. P., Pizzuti A., et al., *Variation of the CGG Repeat at the Fragile X Site Results in Genetic Instability: Resolution of the Sherman Paradox*, Cell, December 1991; 1047-58, hereinafter referred to as "Fu"). The inventors herein investigated a connection between the FMR1 gene and ovarian function based on the distribution peak at $CGG_{n=29\text{-}30}$. Ovarian effects of the FMR1 gene are supported by a known association between FMR1 genotypes in the premutation range ($CGG_{n\sim55\text{-}200}$) and primary ovarian insufficiency (POI), also known as premature ovarian failure (POF) (see, Gleicher N., Weghofer A., Barad D. H., *Defining Ovarian Reserve to Better Understand Ovarian Aging*. Reproductive Biology and Endocrinology, February 2011, 23, hereinafter referred to as "Gleicher I"). A recent study of a mouse FMR1 homologue also supports the association of the FMR1 gene with ovarian aging (see, Hoffman G. E., Le W. W., Entezam A., et al. *Ovarian Abnormalities in a Mouse Model of Fragile X Primary Ovarian Insufficiency*. The Journal of Histochemistry and Cytochemistry, June 2012, 439-56).

Based on their research, the inventors defined new ranges of CGG repeats on the FMR1 gene relevant to ovarian health: a normal (norm) range of $CGG_{n=26\text{-}34}$, a low range of $CGG_{n<26}$ and a high range of $CGG_{n>34}$. Further refinement of these ranges defined norm (both alleles in normal range), heterozygous (het, one allele in and the other outside normal range) and homozygous (hom, both alleles outside normal range) genotypes. Het and hom genotypes were further subdivided into high or low. For example, a female with a het-high genotype has one FMR1 allele with more than 34 CGG repeats and one FMR1 allele with between 26-34 CGG repeats. Cross-sectional studies demonstrate associations between the various genotypes described above and specific ovarian aging patterns (see, Gleicher N., Weghofer A., Barad D. H., *Ovarian reserve Determinations Suggest New Function of FMR1 (Fragile X Gene) in Regulating Ovarian Ageing*. Reproductive Biomedicine Online, June 2010, 768-75, hereinafter referred to as "Gleicher II"; Gleicher N., Weghofer A., Lee I. H., Barad D. H., *FMR1 Genotype With Autoimmunity-Associated Polycystic Ovary-Like Phenotype and Decreased Pregnancy Chance*. PloS One, December 2010, e15303, hereinafter referred to as "Gleicher III"; Gleicher N., Weghofer A., Lee I. H., Barad D. H., *Association of FMR1 Genotypes With in Vitro Fertilization (IVF) Outcomes Based on Ethnicity/Race*, PloS One, April 2011, e18781, hereinafter referred to as "Gleicher IV"; and Gleicher N., Weghofer A., Kim A., Barad D. H., *The Impact in Older Women of Ovarian FMR1 Genotypes and Sub-Genotypes on Ovarian Reserve*, PloS One, March 2012, e33638, hereinafter referred to as "Gleicher V"). These associations are more fully disclosed herein. Genotype/phenotype interactions are usually studied in homozygous subjects, but these studies have so far only studied norm and het women because all three hom sub-genotypes (high/high, high/low and low/low), combined, occur in less than 10 percent of women, not enough to fully study (see, Gleicher II, Gleicher III, Gleicher IV and Gleicher V). These new range and genotype definitions allow the use of the FMR1 gene to assess ovarian health.

Human females are typically tested to determine ovarian health and to assess their fertility only if they are experiencing infertility, at risk for infertility based on age and/or are indicated to have ovarian aging by showing signs of ovarian aging. These tests are for anti-Müllerian hormone (AMH) and/or follicle stimulating hormone (FSH) levels. Tests for FSH levels include tests for estradiol levels because a high estradiol level can suppress FSH levels. Such combined tests are referred herein to as FSH tests or FSH/estradiol tests. The tests are performed once and the human female's level of AMH and/or FSH is compared against the normal range for human females of her age. If AMH is lower than the normal range or FSH and/or estradiol is higher than normal the normal range, the human female is considered to have premature ovarian aging (POA), also known as occult premature ovarian insufficiency (OPOI). These AMH/FSH tests, however, are generally not performed in young human females, defined herein to mean human females who have not experienced infertility and are not otherwise indicated to have ovarian aging.

Because testing for ovarian health is presently performed only when the human female already experienced infertility and/or is indicated for ovarian aging by symptoms, such as menstrual irregularities, the diagnosis of POA or POF is usually only obtained when the POA is at advanced clinical stages, POF has occurred or the human female is about 38 years or older. As a result, there is an absence of prospective risk assessments in adolescent and young adult females even though approximately 10% of human females will suffer from premature ovarian aging. At advanced clinical stage or advanced age, even advanced fertility treatments for POA demonstrate only limited success, and egg donation remains the only realistic choice for women with POF (see, Gleicher I). Late diagnosis, of course, assumes further significance in older, often single women because POA further compounds the negative effects of advanced age. As a result, late diagnosis of POA leads to limited success in treatment.

Earlier diagnosis of premature ovarian aging presents many benefits for women, most notably, earlier and potentially more effective treatment options (see, Cil A. P., Bang H., Oktay K., *Age-Specific Probability of Live Birth With Oocyte Preservation: An Individual Patient Data Meta-Analysis*, Fertility and Sterility, August 2013, 492-9). Identification of human females likely to be affected by POA when their ovarian reserve (OR) is still relatively normal offers a choice between childbirth at a younger age than they otherwise planned or fertility preservation by assisted reproductive technologies. All methods of fertility preservation are more efficient at younger than older ages and, therefore, less costly and more cost-effective. The reduced cost is especially important given ever-increasing medical costs and the present high cost of infertility testing and treatment, which, in many cases, is not covered by health insurance.

Fertility preservation for young women is relatively recent and resulted from a need by women who became infertile after undergoing cancer treatment but who still desired to have children. Fertility preservation emerged to provide young cancer survivors a reproductive future (see, Waimev K. E., Duncan F. E., Su H. I., Smith K., Wallach H., Jona K., Coutifaris C., Gracia C. R., Shea L. D., Brannigan R. E., Chang R. J., Zelinski M. B., Stouffer R. L., Taylor R. I., Woodruff T. K., *Future Directions in Oncofertility and Fertility Preservation: A Report From the 2011 Oncofertility Consortium Conference*, Journal of Adolescent and Young Adult Oncology, March 2013, 25-30). Aside from fertility preservation for cancer patients, women are delaying childbirth for various social and personal reasons and use fertility preservation to have children later in life (see, Donnez J., *Introduction: Fertility Preservation, from Cancer to Benign Disease to Social Reasons: The Challenge of the Present Decade*, Fertility and Sterility, May 2013, 1467-1468; and Cobo A., Garcia-Velasco J. A., Domingo J., Remohl J., Pellicer A., *Is Vitrification of Oocytes Useful for Fertility Preservation for Age-Related Fertility Decline and in Cancer Patients?* Fertility and Sterility, May 2013, 1485-1495). Fertility preservation in response to causes of infertility other than cancer or voluntary delay, such as endometriosis, is also entering medical practice (see, Bedoschi G., Turan V., Oktay K., *Fertility Preservation Options in Women with Endometriosis*, Minerva Ginecologica, April 2013, 99-103). However, fertility preservation in response to other causes of infertility, such as premature ovarian aging, has not yet received attention because premature ovarian aging was not predictable by the existing knowledge in the art.

Ovarian aging is the combination of declines in oocyte quality and oocyte number. Ovulation, the maturation and release of oocytes, begins at menarche, the onset of menstrual cyclicity. Menarche is the start of a complex process of steady follicle recruitment that organizes recruited follicles into maturing monthly cohorts, groups of follicles in the same stage of development. In natural ovulation cycles, follicular cohorts mature over 2-4 months, resulting in ovulation of a single dominant follicle. The other follicles in the cohort undergo degeneration and apoptosis (see, FIG. 1), resulting in unifollicular ovulation. The ovary's ability to organize cohesive monthly cohorts of follicles of similar sizes and maturity is a characteristic of young age and normal ovarian function. The ability to organize and carry out monthly unifollicular ovulation diminishes with advancing female age and/or in association with POA (and possibly early stages of POF). Older females and patients with POA have more inhomogeneous follicle sizes and oocyte maturity distribution than females who are young and not experiencing POA. This difference is shown in IVF studies for those two populations (see, Gleicher I).

As FIG. 1 also shows, the current medical understanding holds that females are born with a limited pool of follicles, also known as the total ovarian reserve (TOR), that depletes throughout life until menopause. TOR peaks in intrauterine life at approximately 7 million follicles/oocytes, with significant depletion before birth. Females have less than 1 million follicles/oocytes at birth and by menarche approximately only 400,000 remain in the female. The speed of ovarian depletion slows between menarche and menopause, when only a few hundred to one thousand follicles/oocytes remain in the ovaries (see, Gleicher I).

A patient's TOR is primarily the large pool of unrecruited, primordial follicles "resting" at a very primitive stage. A patient's recruited follicles (also called "growing" follicles) are a much smaller part of TOR known as the functional ovarian reserve (FOR). After weeks to months of maturation, the recruited follicles reach maturity in either natural or ovarian stimulation cycles. A patient's TOR and FOR deplete over time and reflect the patient's ovarian age.

The genetic basis of follicle recruitment and its effect on TOR and FOR are not completely understood. The genes involved in follicle recruitment appear to limit over-recruitment of primordial follicles, which can rapidly deplete unrecruited follicles. When genes that affect follicle recruitment in either rodents or humans are mutated, blocked or knocked out, primordial follicles are over-recruited and deplete rapidly. Genes involved in follicle recruitment also influence a female's age at menopause. The primary function of these genes, therefore, appears to reduce the rate of follicular recruitment. Slower recruitment preserves more follicles/oocytes, leading to better remaining TOR at later ages.

The speed of follicle recruitment is statistically correlated to the number of remaining primordial follicles. Therefore, the size of the pool of growing follicles (representing FOR) also correlates with speed of recruitment (see, Gleicher V; Gleicher I; and Nelson S. M., Anderson R. A., Broekmans F. J., Raine-Fenning N., Fleming R., La Marca A., Anti-Müllerian Hormone: *Clairvoyance or Crystal Clear*? Human Reproduction, March 2012, 631-636, hereinafter referred to as "Nelson I"). AMH is produced in the granulosa cells of these small growing follicles and inhibits follicle recruitment and growth (see, Gleicher I; Ledger W. L., *Clinical Utility of Measurement of Anti-Müllerian Hormone in Reproductive Endocrinology*. Journal of Clinical Endocrinology & Metabolism, December 2010, 5144-5154, hereinafter referred to as "Ledger"; and Gleicher N., Weghofer A., Barad D. H., *The Role of Androgens in Follicle Maturation and Ovulation Induction: Friend or Foe of Infertility Treatment*? Reproductive Biology and Endocrinology, August 2011, 116). Because of this connection between AMH and the small growing follicles, a human female's AMH levels reflect the size of her pool of small growing follicles. Age-specific AMH levels, which reflect age-specific follicle pool size, are known in the art (see, Barad D. H., Weghofer A., Gleicher N., *Utility of Age-Specific Serum Anti-Müllerian Hormone Concentrations*, Reproductive Biomedicine Online, March 2011, 284-291, hereinafter referred to as "Barad"; and Kelsey T. W., Wright P., Nelson S. M., Anderson R. A., Wallace W. H. B., *A Validated Model of Serum Anti-Müllerian Hormone from Conception to Menopause*, PLoS One 2011, e22024, hereinafter referred to as "Kelsey").

Additionally, the gene that controls the AMH type II receptor (AMHR2) is also associated with follicle recruitment, further connecting AMH to follicle recruitment (see, Voorhuis M., Broekmans F. J., Fauser B. C., Onland-Moret N. C., van der Schouw Y. T., *Genes Involved in Initial Follicle Recruitment May be Associated With Age at Menopause*, Journal of Clinical Endocrinology & Metabolism, March 2011, 473-479). Because of the connection of AMH to follicular recruitment and growth, AMH levels are widely considered to best reflect TOR (see, Ledger; Nelson I). Because TOR is the primary component of ovarian age, low AMH levels are indicative of ovarian aging and AMH levels below normal for a particular age are indicative of premature ovarian aging.

Because of the association of AMH with FOR and TOR, an AMH test with levels below age-specific normal levels can indicate POA. As discussed above, POA affects approximately 10% of all women, and can have different causes, including, but not limited to, the factors set forth in Table 1:

TABLE 1

KNOWN CAUSES OF PREMATURE OVARIAN AGING

Low number of follicles/oocytes at birth/menarche
Known genetic causes
Excessive follicle recruitment
Anti-ovarian autoimmunity
Autoimmune oophoritis
Anti-ovarian autoimmunity Autoimmune polyglandular syndromes
Turner syndrome
Space occupying lesions Endometriosis
Ovarian tumors
Iatrogenic interventions Surgery
Chemotherapy
Radiation therapy
Bone marrow transplantation
Anti-viral therapies As Table 1 shows, aside from iatrogenic (caused by medical treatment) follicle/oocyte losses and ovarian tissue loss from space-occupying lesions, premature ovarian aging has other causes, such as excessively rapid recruitment of follicles, low follicle numbers at birth and/or menarche, genetic disorders and anti-ovarian autoimmunity. Both low follicle numbers at birth and excessively rapid recruitment are under strong genetic control. The other major causes of POA, as discussed below, are also under genetic control.

Approximately one-third of POA cases are caused by anti-ovarian autoimmunity (see, Gleicher N., Weghofer A., Oktay K., Barad D., *Do Etiologies of Premature Ovarian Aging (POA) Mimic Those of Premature Ovarian Failure (POF)*? Human Reproduction, October 2009, 2395-2400). Anti-ovarian autoimmunity is well-known in humans with Addison's disease who develop autoimmune (lymphocytic) oophoritis, autoimmune polyglandular syndromes (APS), and Turner's syndrome. (see, Hoek A., Schoemaker J., Drexhage H. A., *Premature Ovarian Failure and Ovarian Autoimmunity*, Endocrinology Review, February 1997, 107-134, referred to hereinafter as "Hoek"). Hoek also reveals that ovaries are often subject to an autoimmune attack that is statistically associated with thyroid autoimmunity, anti-adrenal autoimmunity and other, often non-organ-specific, autoimmune responses. The X chromosome's role as an autoimmune chromosome also explains the association of autoimmunity and Turner syndrome (see, Bianchi I., Lleo A., Gershwin M. E., Invernizzi P., *The X Chromosome and Immune Associated Genes*, Journal of Autoimmunity, May 2012, 187-192; Bukalov V. K., Gutin L., Cheng C. M., Zhou J., Sheth P., Shah K., Arepalli S., Vanderhoof V., Nelson L. M., Bondy C. A., *Autoimmune Disorders in Women with Turner Syndrome and Women with Karyotypically Normal Primary Ovarian Insufficiency*, Journal of Autoimmunity, June 2012, 315-322; and Lleo A., Moroni L., Caliari L., Invernizzi P., *Autoimmunity and Turner's Syndrome*, Autoimmune Review, May 2012, 538-543). Therefore, autoimmune attacks on the ovaries are known in the art, but their precise mechanisms are not well understood.

Autoimmune-associated premature ovarian aging is most understood in combination with autoimmune polyendocrine syndrome type 1 (APS-1), also known as polyendocrinopathy candidiasis ectodermal dystrophy or Whitaker syndrome. It is caused by a mutation in the autoimmune regulator (AIRE) gene (see, Michels). This gene is of crucial importance in the thymus, where it regulates the process that prevents T cells from attacking a human's own cells. AIRE mutations that interfere with normal AIRE activity are associated with attacks against a human's own cells. The connection between AIRE and premature ovarian aging is supported by animal models. AIRE gene knockout mice experience early follicle depletion by age 20 weeks and complete follicle depletion (POF/POI) in 50-60% of animals. Therefore, AIRE appears crucial for preventing premature ovarian aging, and mutations in the gene de-inhibit follicle maturation, leading to the rapid depletion discussed above. Because of AIRE's strong association with autoimmunity, impaired fertility in the AIRE knockout mouse model can be attributed to immune-mediated loss of TOR. Such immune-mediated loss of TOR is caused by autoimmune attacks on the ovaries, thereby destroying the oocyte reserve. The AIRE gene is the first gene associated with autoimmune-induced premature ovarian aging (see, Michels; and Cushman R. A., *Evidence That the Autoimmune Regulator Gene Influences Thymic Production of Ovarian Antigens and Prevents Autoimmune-Mediated Premature Reproductive Senescence*, Biology of Reproduction, April 2012, 109).

Because of the link between autoimmunity and ovarian aging, any autoimmunity in females must be considered a risk factor for premature ovarian aging. Moreover, because autoimmunity is highly familial, a patient's family history of autoimmunity is also a risk factor. This includes a familial history of repeated pregnancy loss, often the consequence of abnormal immune system activation.

In addition to familial autoimmunity, other genetic influences on ovarian aging are well demonstrated. Age at menopause is well-correlated between mothers and daughters and between pairs of sisters (see, van Asselt K. M., Kok H. S., Pearson P. L., Dubas J. S., Peeters P. H., Te Velde E. R., van Noord P. A., *Heritability of Menopausal Age in Mothers and Daughters*, Fertility and Sterility, November 2004, 1348-1351; and Morris D. H., Jones M. E., Schoemaker M. J., Ashworth A., Swerdlow A. J., *Familial Concordance for Age at Natural Menopause; Results From the Breakthrough Generations Study*, Menopause, September 2011, 956-961). Additionally, age at menarche, which is also genetically influenced, relates to risk for POA (see, Weghofer A., Kim A., Barad D. H., Gleicher N., *Age at Menarche: A Predictor of Diminished Ovarian Function*, Fertility and Sterility, October 2013, 1039-1043). Therefore, whether a human female's mother or sister(s) entered menopause early and/or a human female's own young age at menarche should also be considered risk factors for POA.

All of the publications mentioned above, as well as those mentioned below, are incorporated by reference herein.

SUMMARY OF THE INVENTION

A method for early detection of risk of infertility and premature ovarian aging in and treatment of a human female who has not experienced infertility and is not otherwise indicated to have premature ovarian aging involves performing an FMR1 gene test on such human females to assess whether premature ovarian aging is likely to occur in said females in the near future, usually within 3 to 8 years. The articles entitled *FMR1 Gene Mutations Already at Young Ages Are Predictive Of Later Premature Ovarian Senescence and Infertility* (Kushnir V. A., Yao Y., Himaya E., Barad D. H., Weghofer A., Lee H. J., Wu Y. G., Shohat-Tal A., Lazzaroni-Tealdi E., Gleicher N., *FMR1 Gene Mutations Already at Young Ages Are Predictive Of Later Premature Ovarian Senescence and Infertility*, 2013, hereinafter referred to as the "longitudinal study" and included as Appendix A) and *A New Paradigm in Adolescent and Young Adult Gynecology: Prospective Risk Assessment for Premature Ovarian Senescence in High-Risk Females* (Gleicher N., Kushnir V. A., Barad D. H., *A New Paradigm in Adolescent and Young Adult Gynecology: Prospective Risk Assessment for Premature Ovarian Senescence in High-Risk Females*, 2013, hereinafter referred to as the "paradigm study" and included as Appendix B) are incorporated by reference in their entirety.

As used herein, a human female who has not experienced infertility is defined as a human female who has not attempted to become pregnant for at least one year and failed to become pregnant during that year. Of course, a human female who has not even attempted to become pregnant is also defined as not having experienced infertility. As used herein, a human female that is not indicated to have ovarian aging is defined as a human female who is less than 28 years old, has not experienced infertility and has not entered menopause.

As discussed in the detailed description of the invention, a human female's FMR1 genotype indicates her risk of premature ovarian aging. When the FMR1 test indicates that the human female is at risk of premature ovarian aging, a regimen of repeated secondary tests of a hormone related to fertility at short intervals is performed on such human females. As used herein, a hormone related to fertility means any hormone known to be related to fertility, including, without limitation, AMH, FSH and estradiol. AMH and FSH are used as exemplar hormones related to fertility herein. As used herein, short intervals means repeating one or more of the secondary tests at set times during the three to eight year period, e.g., at the end of every six month interval, at the end of every yearly interval or at the end of every interval of another length.

This testing regimen is determined by initial AMH/FSH testing to determine whether the human female's level of the hormone being tested is outside the normal range for human females of her age or within the normal range for human females of her age. The normal range for a human female of a particular age is defined as within a particular confidence interval within the average level for a human female of that age. The confidence interval may be, without limitation, a 95% confidence interval, a 75% confidence interval or any confidence interval selected as the limit of the normal range of levels of that hormone for a human female of that age. When the level of the hormone is outside the normal range for a human female of that age, the human female is considered to have premature ovarian aging. When the level of the hormone is in the normal range, the regimen of repeated AMH/FSH tests at set intervals begins. The length of the intervals between tests is determined by the female's level of the tested hormone. A short interval is used if the female's level of the tested hormone trends strongly to the top or bottom of the normal range, depending on the tested hormone, and a longer interval is used if the female's level of the hormone being tested is within the mid-range of the normal range. A female's level of the tested hormone is defined as tending strongly to the top or bottom of the normal range if it is outside a particular confidence interval for the average level for a human female of that age. The confidence interval that defines a human female as tending strongly to the top or bottom of the normal range may be the 68% confidence interval or any other confidence interval within the normal range of range of levels of the hormone being tested for a human female of that age that is selected as the level at which a human female is tending strongly to the top or bottom of the normal range of levels of that hormone for a human female of that age.

Importantly, the combination of the results of the FMR1 and AMH/FSH tests are used to determine whether to treat the human female. For example, when the results of the AMH/

FSH test that are performed as a result of the FMR1 test, indicate AMH/FSH levels outside of the normal range for a human female of the same age, infertility treatments are provided to the human female. Additionally, or alternatively, the human female may have oocytes removed and frozen for IVF procedures at later times. Additionally, the human female may be notified in writing or electronically of a detected possibility of premature ovarian aging and increased risk of infertility and instructed to take action to address this situation.

BRIEF DESCRIPTION OF THE DRAWINGS

FIG. 6 is a table of parameter estimates calculated by analysis of covariance (ANCOVA) of AMH baselines of the donors in the longitudinal study, showing the associations between the FMR1 genotypes and ovarian aging;

FIG. 7 is a table of parameter estimates calculated by a generalized estimating equation (GEE) of AMH assessments in the donors in the longitudinal study, showing the associations between the FMR1 genotypes and ovarian aging;

FIG. 8 is a table of estimates calculated by a linear mixed-effects fixed effect model of AMH assessments in the donors in the longitudinal study, showing the associations between the FMR1 genotypes and ovarian aging;

FIG. 13 is a table summarizing all pairwise comparisons of ∆ AMH between pairs of FMR1 genotypes.

DETAILED DESCRIPTION OF THE INVENTION

The present invention relates to a method of early detection, testing and treatment of ovarian aging in a human female who has not experienced infertility and is not otherwise indicated to have premature ovarian aging, and to a method for predicting infertility of such a human female. The method is based on the results of the longitudinal study explained with reference to FIGS. 4-13. This study examined longitudinal data, i.e., data taken from the same subjects over a multi-year period, relating hormone levels in human females to the status of alleles of the FMR1 genes of those human females. Based on the longitudinal data of the study, novel techniques have been developed to tailor treatment and testing regimens for human females who have not experienced infertility and are not otherwise indicated to have premature ovarian aging, but nonetheless are at risk for imminent premature ovarian aging or infertility.

The longitudinal data in the study relates to the association of low alleles of the FMR1 gene, characterized by $CGG_{n<26}$ and carried by approximately one-quarter of all females, with premature ovarian aging and female infertility. Females carrying such alleles can now be identified at young ages as at risk for imminent premature ovarian aging and infertility. Such women can then undergo specific treatment and/or testing regimens, based on their FOR, until a diagnosis of premature ovarian aging is either confirmed or refuted by additional hormonal testing. Those women whose deviation from normal levels of FOR is confirmed can be counseled at young ages when fertility preservation is more efficient, effective and less costly than in older women. This provides such women options of advancing pregnancies or of pursuing fertility preservation by oocyte and/or ovary freezing at younger ages than currently performed. Accordingly, fertility outcomes are improved.

By analyzing the FMR1 genes of young human females, young human females can be identified as at risk of premature ovarian aging and/or infertility and a hormone testing regimen based on the young human females' FMR1 genotypes can be performed. If the testing indicates that the young human female has premature ovarian aging, the young human female can then be treated. The treatment for premature ovarian aging may be any treatment or treatments for a human female that has experienced infertility or is at risk for infertility based on age, even though the human female does not currently exhibit such infertility. Examples of such treatment are disclosed in Gleicher II, Gleicher III, Gleicher IV and Gleicher V and other references mentioned herein.

Figure 3:
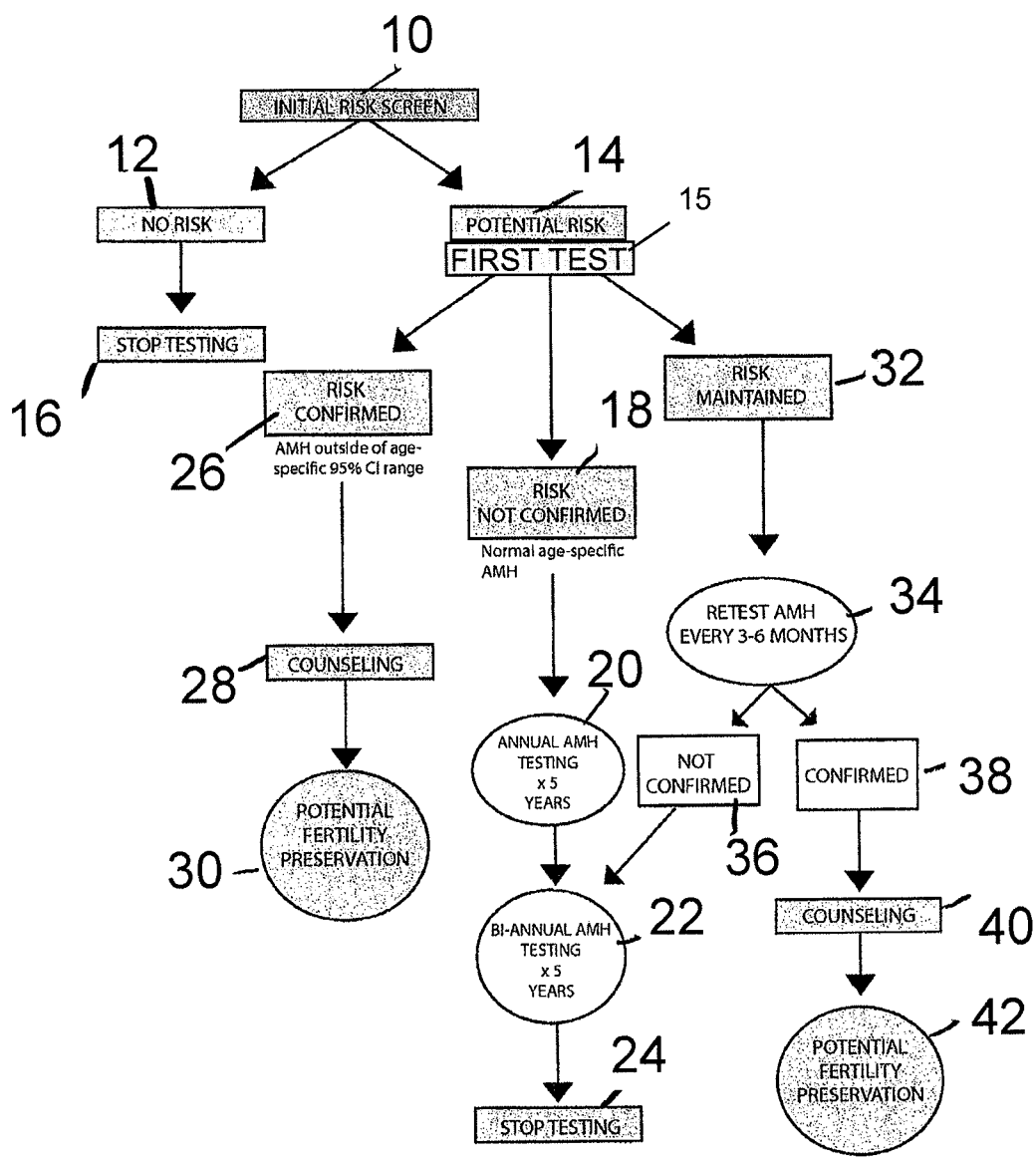
FIG. 3 is a flow chart of a screening, testing and treatment method in accordance with an embodiment of the invention.

Referring now to FIG. 3, FIG. 3 is a flow chart explaining the steps in a screening, testing and treatment method in accordance with the invention. As a first step, an initial risk screening 10 for women who have not experienced infertility and are not otherwise indicated to have premature ovarian aging. Each woman is questioned about diagnosis and risk factors affecting ovarian health, and an examination performed. All of the diagnoses in Table 1 and certain risk factors predispose a young woman towards POA. Examples of risk factors are set forth in Table 2:

TABLE 2

RISK FACTORS FOR PREMATURE OVARIAN AGING

Iatrogenic factors

Ovarian surgery
Chemotherapy
Radiation therapy
Bone marrow transplantation
Anti-viral therapies
Other medical risk factors Endometriosis
Polycystic ovarian syndrome (PCOS)
FMR1 mutations het-norm/low sub-genotype
hom/low/low sub-genotype
BRCA1 mutations
Turner syndrome

TABLE 2-continued

RISK FACTORS FOR PREMATURE OVARIAN AGING

Autoimmunity

Thyroid autoimmunity
Adrenal autoimmunity
Any other autoimmunity
Autoimmune polyglandular syndromes
Family history of autoimmune disease
(One $1^{st}$ degree or two $2^{nd}$ degree relatives)
History of repeated pregnancy loss
History of early maternal/sibling menopause The presence of multiple risk factors multiplies overall risks. Each listed risk factor, on its own, warrants inclusion of a young woman into a prospective risk-screening program. Moreover, even if risk of premature ovarian aging and/or infertility is first established after age 21, the woman should be entered into a prospective risk-screening program.

As part of the initial risk screening 10, an FMR1 test is performed. An FMR1 gene is isolated from the human female and assayed in a manner known to those skilled in the art to determine the number of CGG repeats on each allele of the isolated FMR1 gene. Examples of assays available for use in the invention include, but are not limited to, Southern blotting and polymerase chain reaction.

The number of CGG repeats on both alleles of the FMR1 gene is used to determine the primary basis for assigning the human female to a "no risk" category 12 or to a "potential risk" category 14. In the latter case, additional testing 15, 20, 22, 34 and treatment based on the testing may be performed. Such additional testing may be testing of any hormone known to indicate FOR, such as levels of AMH and/or FSH. Additional testing and subsequent treatment is not automatically performed for every human female who undergoes the FMR1 genetic testing. A young human female having an age range of about 21 years to about 28 years who has not experienced infertility and is not otherwise indicated to have premature ovarian aging is not automatically treated for premature ovarian aging or infertility. Rather, young human females are divided into "no risk" 12 and "potential risk" 14 categories based on the initial risk screening 10, which optimizes the additional testing 15, 20, 22, 34 and treatment for young human females and directs such testing and treatment to those human females at a higher risk for premature ovarian aging. Because the tested human females are usually young, have not experienced infertility and are not otherwise indicated to have premature ovarian aging, treatment for ovarian aging is not commonly prescribed for such human females.

The criteria for additional testing for the human female depends upon the determined number of CGG repeats on at least one of the alleles of the FMR1 gene being less than 26. In one embodiment, the human female is classified as at potential risk 14 and the additional testing for the human female is performed only when the determined number of CGG repeats on only one of the allele of the FMR1 gene is less than 26, but not both. Subsequent treatment is provided to the human female based on the results of the additional testing.

For young human females determined to have an FMR1 gene with CGG repeats on both of the alleles of the FMR1 gene is not less than 26, i.e., in a normal range of 26 to 34 or in a high range above 34, the additional testing and subsequent treatment is not performed because for these human females, the risk of premature ovarian aging is not statistically significant. For these women in the "no risk" category 12, testing ceases at 16. For women in the "potential risk" category 14, additional testing is performed to assess the degree of risk, i.e., whether premature ovarian aging has occurred or is imminent and/or to provide a prediction of infertility.

The additional testing performed when the number of CGG repeats on at least one of the alleles of the FMR1 gene is less than 26 may take various forms, including testing various hormone levels related to fertility. Each test is designed to assess FOR markers. In one embodiment, the human female's serum level of AMH and/or the human female's serum level of FSH is measured in the first testing 15. A determination is made whether the serum level of AMH is normal or less than a selected confidence interval for a human female of the age of the female at the time of the measurement or the serum level of FSH is normal or greater than a selected confidence interval for a human female of the age of the female at the time of the measurement. In one embodiment, the selected confidence interval is a 95% confidence interval. Confidence intervals for AMH and FSH levels at particular ages are known in the art and appear in published sources, e.g., Gleicher II, Gleicher III, Gleicher IV and Gleicher V and other references mentioned herein.

While AMH results are widely considered a stable indicator of FOR, reproducibility of results with currently available tests has recently been questioned (see, Anderson R. A., Nelson S. M., Wallace W. H., *Measuring Anti-Müllerian Hormone for the Assessment of Ovarian Reserve: When and for Whom is it Indicated?*, Maturitas, January 2012, 28 hereinafter referred to as "Anderson"; and Fleming). Moreover, AMH levels might be influenced by hormonal contraceptives and unstable during the menstrual cycle (see, Kallio S., Puurunen J., Ruokonen A., Vaskivuo T., Piltonen T., Tapanainen J. S., *Antimüllerian Hormone Levels Decrease in Women Using Combined Contraception Independently of Administered Route*, Fertility and Sterility, April 2013, 1305-1310; Robertson D. M., Hale G. E., Fraser I. S., Hughes C. L., Burger H. G., *Changes in Serum Antimüllerian Hormone Levels Across the Ovulatory Menstrual Cycle in Late Reproductive Age*, Menopause, May 2011, 521-524; and Hadlow N., Longhurst K., McClements A., Natawala J., Brown S. J., Matson P. L., *Variation in Antimüllerian Hormone Concentration During Menstrual Cycle May Change the Clinical Classification of the Ovarian Response*. Fertility and Sterility, May 2013, 1791-1797). Because of this new uncertainty, if the first test 15 is an AMH test, two or more consecutive AMH evaluations should be conducted as the first test 15, approximately one month apart. If these tests show similar AMH levels, then further treatment and testing would be based thereon. In addition, any time a test is described as being performed in the method, it should be understood that this test may not be a single test but may be a plurality of tests to minimize errors or deviations in a single test due to variations in the human female's hormone levels due to her menstrual cycle, contraception or any other reasons. Additionally, tests of other hormones than the initially tested hormone may be performed to confirm the findings of the initial test. Thus, the AMH/FSH testing as used herein means to perform one or more of the same tests or one or more of different tests seeking the same objective or results.

If, in the first test 15, the young human female is determined to have normal age-specific AMH/FSH levels, the human female is categorized as "risk not confirmed" 18. Annual repeat testing 20 for AMH/FSH levels is conducted, e.g., for practical timing purposes in association with annual PAP smears. After 3-5 years of such annual testing 20, if the AMH/FSH levels are still age-specific, mid-range, the female may be switched to a regimen of biennial testing 22. If after 5-8 years of biennial testing 22, there is again no deviation of AMH/FSH from standard age-specific levels, testing may be stopped 24.

If the young human female is determined in the initial additional testing 15 to have a serum level of AMH less than a 95% confidence interval or a serum level of FSH greater than a 95% confidence interval for a human female of her age then she is considered to be "risk confirmed" 26, and the woman is directed to counseling 28 and potential fertility preservation 30. This woman is considered a prime candidate for treatment for imminent premature ovarian aging and at risk for infertility.

If the young human female is determined in the first test 15 to have a serum level of AMH/FSH that is within the 95% confidence interval for that hormone but that trends towards the border of that confidence interval, the woman is considered "risk maintained" 32. Such women, depending on degree of abnormality, have to be more closely followed than those considered "risk not confirmed" 18, and reassessed with repeat AMH/FSH measurements or other FOR assessments at relatively shorter intervals, such as every 3-12 months 34. If this repeated testing 34 indicates that the human female's AMH/FSH levels are outside of the 95% confidence interval for a human female of her age, then the woman's risk is confirmed 38 and she is directed to counseling 40 and potential fertility preservation 42. If the repeated testing indicates that the AMH/FSH levels remain within age-specific levels, then the woman's risk is not confirmed 36, and she is directed to bi-annual testing 22 and possible cessation of testing 24. As used herein, all intervals and/or periods of periodic testing are approximate. A human female undergoing repeated testing at set intervals may undergo each test at a time within 30 days of the end of each interval or period. Additionally, the total period of testing for a human female may be any period between 3 and 8 years, preferably approximately 4 years.

Another consideration of the first test 15 and the repeated testing 20, 22 and/or 34, is the presence of abnormally low or abnormally high AMH levels. Abnormally low AMH levels denote POA, while abnormally high levels often suggest polycystic ovary syndrome (PCOS) (see, Ledger; Nelson I; Barad; Anderson). PCOS has also been associated with increased risk of anti-ovarian autoimmunity and with a quickly depleting ovarian phenotype, leading to early POA in association with low FMR1 alleles (see, Sen A., Kushnir V. A., Barad D. H., Gleicher N., *Endocrine Autoimmune Diseases and Female Infertility*, Nature Reviews Endocrinology, November 2013, In press; and Gleicher III). While POA is usually a slowly progressing loss of FOR, it can be very quick in a small minority of women. Because these women cannot be identified in advance, repeat testing of FOR at short intervals is essential.

If repeated testing 20, 22 and/or 34 demonstrates deviation from normal AMH (or other FOR parameter) aging patterns, a patient can be considered to have a confirmed diagnosis of POA. At this point, a formal consultation or counseling 28, 40 to discuss the significance of this diagnosis for the young woman's reproductive future is offered. In this consultation, fertility preservation 30, 42 by oocyte and/or ovarian cryopreservation may be offered.

Advantages of the invention are the ability to identify high risk women for POA at very young ages (anywhere from 16-28 years old) based on FMR1 genetic testing, a treatment plan for such women and variable and adaptable reproductive plans, including fertility preservation at very young ages. Oocyte and/or embryo cryopreservation is much more efficient and effective and less costly in younger women than in older women. Because the invention allows detection of POA before it occurs, it allows such treatments before the diagnosis of POA, which is usually made at much later stages, i.e., after the woman has experienced infertility.

Approximately 10 percent of all females are affected by POA (see, Gleicher I). Many of those affected will seek infertility treatment. Early diagnosis of impending premature ovarian aging would allow such women to either change their reproductive life schedule and/or take fertility-preserving steps, like oocyte cryopreservation (see, Donnez J., *Introduction: Fertility Preservation, From Cancer to Benign Disease to Social Reasons: the Challenge of the Present Decade*, Fertility and Sterility, May 2013, 1467-8). Both of these options are more patient-friendly, effective and economical than the current practice of treating POA after it is at an advanced stage.

As mentioned above, the foregoing methods are derived from a study that obtained longitudinal FOR data from the same subjects over a period of several years. This particular data allowed for analysis of how the FMR1 genotype is indicative of imminent ovarian aging in human females who have not experienced infertility and are not otherwise indicated to have premature ovarian aging. The data was correlated to progression of ovarian aging over a significant span of a human female's life and enabled highly accurate prediction of the expected onset of ovarian aging. Such accurate prediction allows treatment when ovarian aging is in its early stages or even before it begins to affect a human female's reproductive ability. That is, methods in accordance with the invention, when applied to human females who have not experienced infertility and are not otherwise indicated to have premature ovarian aging, determine the imminence of ovarian aging, i.e., whether it will occur in a period of a few years, such as about 4 years, from an initial assessment of ovarian health, and provide for treatment and/or testing regimens dependent on the determined imminence of ovarian aging.

In addition to the prediction of imminent ovarian aging, the longitudinal data obtained during the study allows for prediction of female infertility. A female is considered infertile after trying and failing to become pregnant for at least a year. Many women who experience infertility have premature ovarian aging. As such, early predictions based on the longitudinal data of the study enabled the development of treatment and/or testing regimens of human females for infertility before they are infertile. An advantage of the invention is that a woman can be forewarned in the event she will likely fail when she attempts to become pregnant and offered fertility treatment much earlier than previously possible.

More particularly, the longitudinal study investigated functional ovarian reserve (FOR), as reflected by AMH levels, relative to FMR1 genotypes/sub-genotypes in 233 consecutive oocyte donor candidates [233 baseline and 122 repeat AMH measurements for a total of 355 measurements] and 354 baseline-AMH measurements from consecutive infertility patients under 38 (mean age 35.5±3.5 years). The 354 infertile women served as a cross-sectional comparison group to assess effects of FMR1 mutations on later occurring female infertility. Sixty-six donors had multiple longitudinal assessments over approximately 4 years, typically at uniform intervals, (e.g., yearly). Donor candidates with presumed increased reproductive risks based on medical, family and genetic histories were excluded.

FMR1 genotypes and sub-genotypes are defined in Gleicher II, Gleicher III, Gleicher IV and Gleicher V. By defining a normal $CGG_{n=26\text{-}34}$ range, all $CGG_n$ below and above that range are considered abnormal. A female with both FMR1 alleles in normal range, therefore, is norm, one with one in and one outside normal range is het and one with both alleles outside norm range is hom. Whether an allele is above (high) or below (low) normal range further sub-divides het and hom genotypes (het-norm/high, het-norm/low, hom-high/high, hom-high/low, hom-low/low) into sub-genotypes. The Table 3 provides the definitions of the terms used herein.

TABLE 3

|  | One Allele | Other Allele | Genotype/ Sub-genotype |
|---|---|---|---|
| (CGG 26 ≤ n ≤ 34 = norm) | High | High | Hom-high/high |
|  | High | Norm | Het-norm/high |
| (CGG n > 34 = high) | High | Low | Hom-high/low |
|  | Norm | Norm | Norm |
| (CGG n < 26 = low) | Norm | Low | Het-norm/low |
|  | Low | Low | Hom-low/low |

The longitudinal study had two purposes. The first purpose was to assess potential impacts of FMR1 genotypes/sub-genotypes on premature ovarian aging, also called occult primary ovarian insufficiency (OPOI) (see, Gleicher I). To avoid contamination by the effects of physiologic ovarian aging, only women infertile women under age 38 years were included in the study. The second purpose was to determine whether differences in distribution of FMR1 genotypes/sub-genotypes between younger oocyte donors and older infertility patients are influenced by the increasing risk of experiencing infertility with advancing age. The 354 consecutive infertility patients below age 38 years (mean age 33.5±3.5 years) served as an older cross-sectional comparative group to assess whether the speed of decline in FOR, as measured by the size of the decreases in AMH (ΔAMH), differed between FMR1 genotypes and sub-genotypes and whether the prevalence of individual FMR1 genotypes and sub-genotypes differed between donor and infertility patient populations.

Briefly, the longitudinal study found that donors with both alleles with a low CGG count ($CGG_{n<26}$) (hom-low/low) demonstrated significantly lower AMH than donors with normal CGG counts (both alleles $CGG_{n=26-34}$, norm). The het-low FMR1 genotype was associated with more rapid declines in AMH than the norm genotype or het-high FMR1 genotype. Δ AMH significantly differed between the young donor subjects and the older infertility subjects and among het-norm/low, norm and het-norm/high populations. The overall distribution of the FMR1 genotypes and sub-genotypes also differed between the young donor subjects and the older infertility subjects. These findings support conditionally limiting the additional testing and treatment for premature ovarian aging and risk of infertility to young human females whose testing shows that have at least one FMR1 allele with less than 26 CGG repeats (the hom high/low, hom low/low and het norm/low FMR1 genotypes).

The longitudinal study assessed effects on FOR of all FMR1 genotypes and sub-genotypes, and enables a novel treatment method. In the longitudinal study, the difference in Δ AMH between young human female donors and older infertility patients was determined for the FMR1 genotypes/sub-genotypes. The longitudinal study showed that the hom FMR1 genotypes and het-low sub-genotypes identify young females at risk for premature ovarian aging. POA is a major cause of female infertility that affects approximately 10% of all women, and is only diagnosed at advanced stages, when potential interventions are less effective and more costly than they would be at earlier stages.

Figures 4, 5:
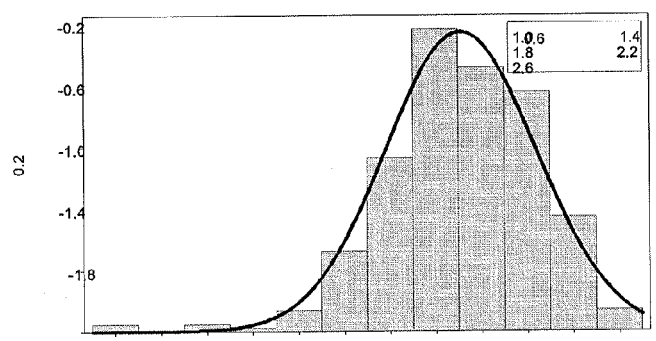
FIG. 4 is a table showing the baseline characteristics and FMR1 genotypes of oocyte donor candidates and infertility patients and distribution of FMR1 genotypes/sub-genotypes in the longitudinal study.
FIG. 5 is a histogram of log(AMH) of the donors in the present study.

FIG. 4 summarizes characteristics of the egg donor subjects (human females that have not experienced infertility and are not otherwise indicated to have premature ovarian aging as defined above) and known infertility patients. The mean age of women at the time of the baseline measurements was 24.4±3.3 years for the egg donors and 33.5±3.5 years for the infertility patients. The age of human females within the donor and infertility patient groups did not vary significantly for different FMR1 genotypes and sub-genotypes. Mean AMH at the baseline measurement was 4.3±2.6 for the donor human females and 1.9±2.1 ng/mL for the infertile patients. Mean body mass indices (BMI) at the baseline measurement were 21.4±2.4 for the donor human females and 24.4±5.5 kg/m$^2$ for the infertile patients.

Baseline AMH values are the values in the initial AMH testing for each subject, performed after their FMR1 gene was isolated and the number of CGG repeats on both alleles of the FMR1 gene were determined. The FMR1 and AMH tests were performed by routine commercial assays, as described in Gleicher II, Gleicher III, Gleicher IV and Gleicher V. The age of each donor/infertile patient was recorded with their first AMH collection. AMH values were logarithmically transformed to satisfy the normality assumption of statistical models, and to obtain a new variable, $\log_{AMH}$, referred to herein as AMH. FIG. 5 shows a histogram for AMH for all 355 donor samples. Repeat AMH tests were performed if a donor was matched with an IVF candidate more than six months after the initial AMH test. Values from these repeat tests were statistically adjusted, including adjustments for age. This provided baseline values for all subjects of the longitudinal study and repeat AMH values for many subjects.

In FIG. 4, the p-value for Age, AMH and BMI is based on two independent sample t-tests of the distribution of means of donors and infertility patients. The p-value for FMR1 n % is based on a chi-square test related to the distribution of FMR1 sub-genotypes of donors vs. infertility patients. The p-values show that the FMR1 sub-genotypes and AMH are strongly correlated.

Donors and infertile patients differed significantly in age, AMH and BMI values (all P<0.001; see, FIG. 4). Low mean AMH and high mean FSH values in the infertile patient group reflect an infertility patient population with very poor fertility characteristics based on those hormone levels. Full ($CGG_{n>200}$) and premutation range alleles ($CGG_{n=55-200}$) were almost absent in both subject groups, with 1 case in each group. The high alleles ($CGG_{n>34}$) in the FMR1 data, therefore, primarily represent CGG values in the ranges $CGG_{n<45}$ or $CGG_{n=45-54}$, and the correlations are not due to FXS, which appears in persons with full mutation range FMR1 genotypes.

The relationship between AMH and FMR1 genotypes/sub-genotypes was examined while accounting for the age variations among the subjects. Repeated AMH measurements, age and FMR1 genotype/sub-genotype were collected from the 233 donor candidates. A generalized estimating equation (GEE) model, using the norm FMR1 genotype as a reference level, was used to study the effect of FMR1 genotypes/sub-genotypes on AMH while accounting for correlations within subjects. A linear mixed-effect (LME) model was used to confirm the results provided by GEE. The results of the GEE and LME models are reported in FIGS. 6-8.

Short-term (approximately 4 years) time-related AMH changes were investigated using a LME model based on repeated AMH measurements in donors. Long-term (approximately 10 years) time-related AMH changes were studied by comparing baseline AMH values between donor candidates and infertility patients. The AMH baseline decline Δ AMH was calculated. Baseline AMH in donors with the norm genotype was higher than in donors with the hom-low/low sub-genotype (P=0.001) but did not differ from other FMR1 sub-genotypes (See, FIG. 6). A statistical comparison of repeated measurements of donor AMH between norm and all other FMR1 sub-genotype using a GEE model revealed a difference between norm and hom-high/high (p<0.001) and hom-low/low (p=0.006) (see, FIG. 7). This conclusion was further confirmed by a linear mixed-effects model.

Figure 9:
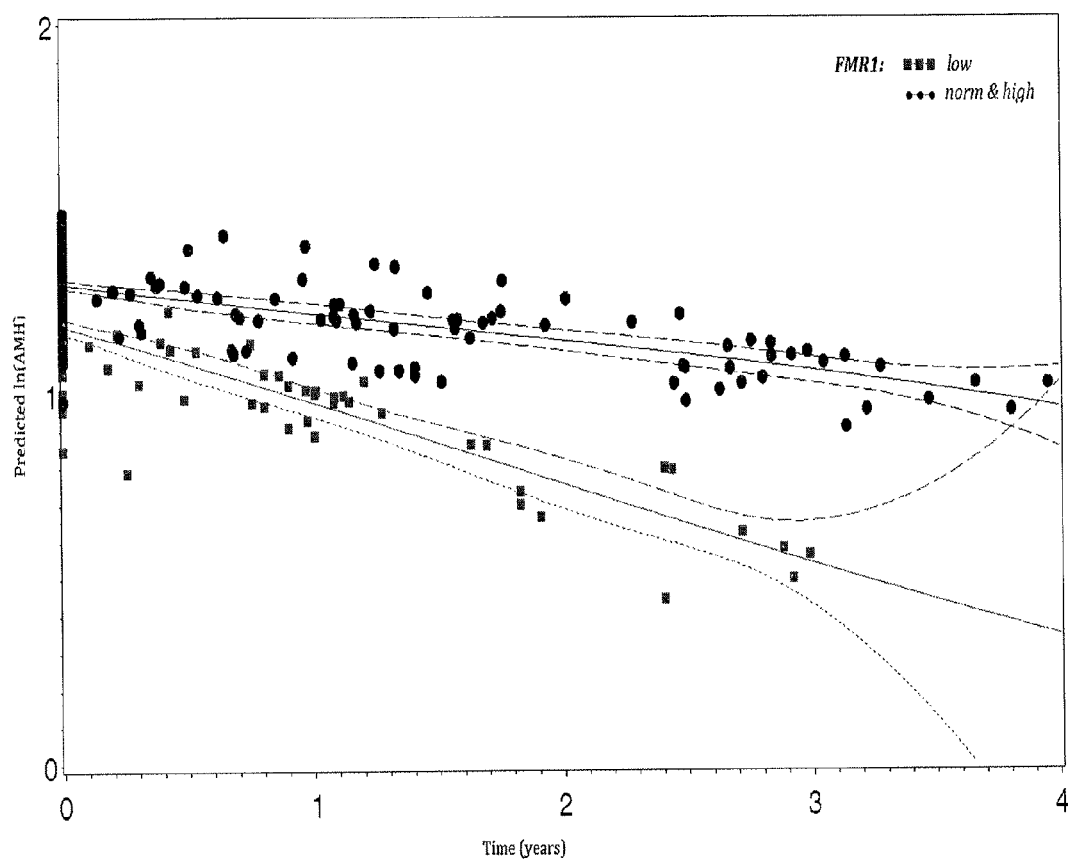
FIG. 9 is a graph of repeat longitudinal AMH measurement in the donors in the longitudinal study separated by FMR1 genotypes/sub-genotype, showing the different patterns of AMH change over time in donors with and without an FMR1 low allele.

The correlation between FMR1 genotype/sub-genotype and change in AMH level over time is statistically significant (P=0.046) (see, FIG. 8). Based on this correlation, a human female's future decline in AMH levels can be predicted based on her FMR1 genotype. FIG. 9 shows the predicted AMH over a 4 year observation period and demonstrates that AMH declines more rapidly in donors with at least one low ($CGG_{n<26}$) allele than in donors with only norm and high alleles. Specifically, FIG. 9 presents the predicted decline of AMH over time for low vs. norm and high genotypes (P=0.046): low sub-genotypes includes het-norm/low, hom-low/low or hom-low/high; high sub-genotypes includes het-norm/high and hom-high/high; and the norm genotype represents a biallelic $CGG_{n=26-34}$.

This decline in AMH in young human females with at least one low allele indicates that additional testing and treatment for premature ovarian aging and risk of infertility is more useful and productive in such young human females than in other young human females. This led to the development of the invention herein, where young human females with at least one low allele of the FMR1 gene are identified and additional testing at set intervals over an extended period of time is performed in said females. The set intervals may be any interval such as six months, one year or two years, and the extended period of time may be any period, such as three to eight years, preferably four years. The additional testing consists of intermittent testing for levels of a hormone, such as AMH and/or FSH, to assess fertility. The human female is then treated when the level of the hormone, such as AMH and/or FSH, indicates risk of infertility or premature ovarian aging. This treatment can therefore be started when the human female is still young, an improvement over the prior art, in which the treatment is performed only after the human female has experienced infertility or premature ovarian aging. Early commencement of infertility treatment improves the likelihood of a successful conception and pregnancy and is not otherwise performed.

Figures 10, 11:
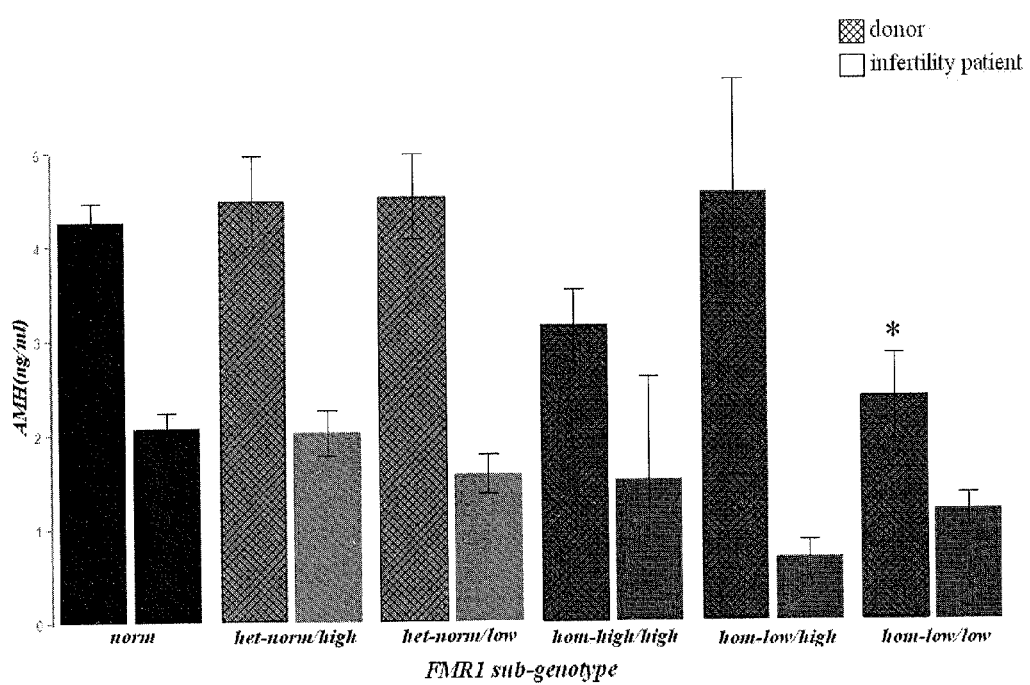
FIG. 10 is a histogram of the prevalence of the FMR1 sub-genotypes in oocyte donors and infertility patients in the longitudinal study.
FIG. 11 is a table showing the mean change in AMH for the subjects with each FMR1 genotype/sub-genotype in the longitudinal study.

Young hom-high/high and hom-low/low donors start out with lower AMH than young norm FMR1 donors. FIG. 10 shows comparative baseline AMH graphs for donors and infertile women, presented as a mean and a standard error of mean. AMH levels decline in all FMR1 genotypes/sub-genotypes between younger oocyte donors and older infertility patients. The decline, however, varies among FMR1 genotypes/sub-genotypes, demonstrating that ovarian aging speed varies based on FMR1 genotypes/sub-genotypes. The statistical comparison of donor AMH baseline between normal alleles and the other FMR1 sub-genotypes, using ANCOVA, showed *P=0.001. The mean and standard deviation of ΔAMH for each FMR1 genotypes/sub-genotypes are summarized in FIG. 11.

Moreover, determination of ΔAMH serves as another basis for treatment of young human females. When the change is higher than the expected change based on the age of the human female, infertility treatment or treatment for premature ovarian aging may be initiated. This aspect of the invention relies on changes in hormone levels to initiate treatment for human females who otherwise would not be expected to receive infertility treatment or treatment for premature ovarian aging.

Figure 12:
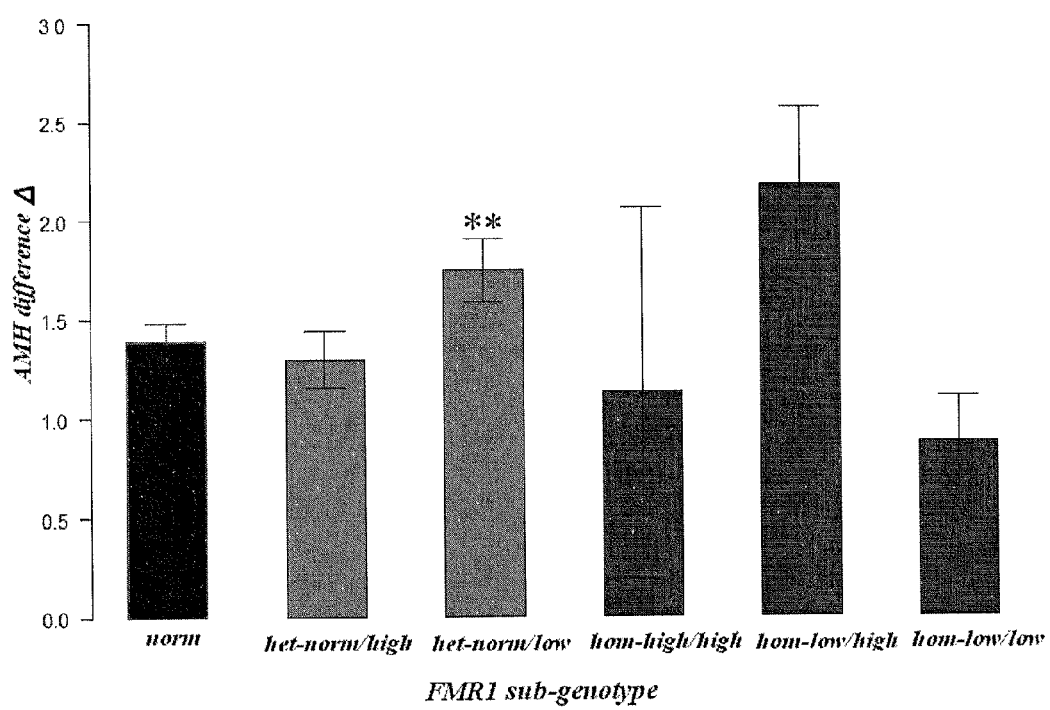
FIG. 12 shows a difference of baseline AMH between oocyte donors and infertility patients.

Because of the small total number of subjects with hom FMR1 genotypes, hom-high/high, hom-high/low and hom-low/low were combined, and ANCOVA was used to compare the distribution between genotypes and remaining het sub-genotypes, demonstrating a statistically significant difference in the decline in A AMH between human females with the het-norm/low sub-genotype and the norm genotype (P=0.045) or the het-norm/high genotype (P=0.042) (see, FIG. 12). The data is presented as a mean and a standard error of mean. The absence of a statistically significant difference between het-norm/low and hom FMR1 sub-genotypes is likely due to the small number of hom sub-genotypes. This is further supported by individual AMH values in the hom-high/low donor group, where AMH was either high or low, resulting in a mean value for all hom-high/low subjects in between these two extremes even though individual human females with the hom-high/low FMR1 genotype did not exhibit such in-between levels. The resulting mean is probably not representative of gene activity.

Figure 1:
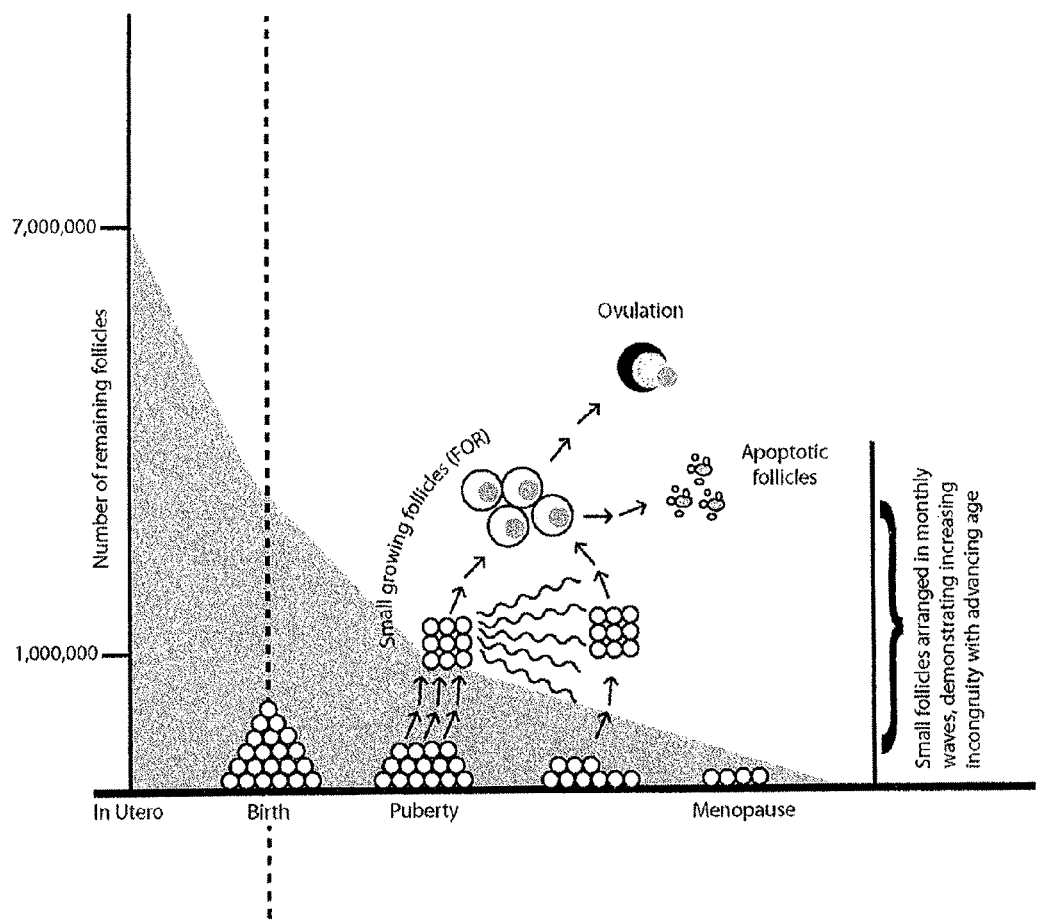
FIG. 1 is a graph depicting the ovulation process and showing the relationship between follicle/oocyte numbers in a human female and her age.
Figure 2:
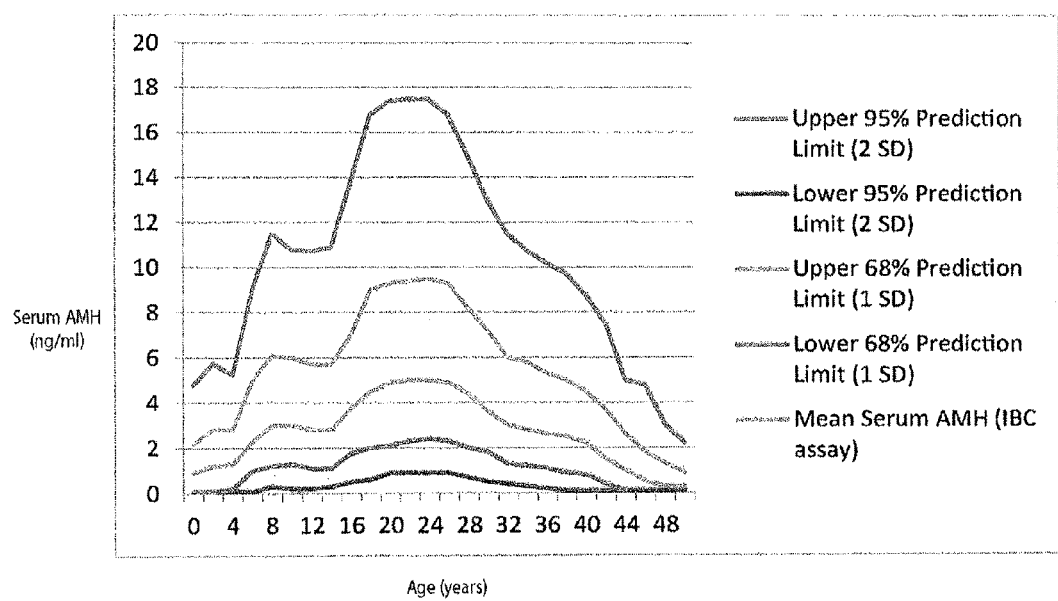
FIG. 2 is a graph of mean AMH levels over time in human females and the upper and lower confidence intervals for AMH levels in human females.

FIG. 13 shows the ΔAMH and the statistical significance of all pairwise comparisons of ΔAMH between the FMR1 genotypes. Decline in FOR, as measured by ΔAMH, is significantly associated with FMR1 low genotypes/sub-genotypes in younger oocyte donors and older infertility patients. More rapid declines in FOR lead to more female infertility and, therefore, either to more or less observed infertility treatments. Fewer infertility treatments will be observed if patients with a particular FMR1 genotype have already dropped out of treatment before inclusion in this study (see, Gleicher N., Weghofer A., Kim A., Barad D. H., *Comparison of Ovarian FMR1 Genotypes and Sub-Genotypes in Oocyte Donors and Infertile Women*, Journal of Assisted Reproduction and Genetics, June 2012, 529-32). The relative absence of infertility patients with the FMR1 low genotypes associated with poor ovarian reserve and poor IVF outcomes in the infertility patients indicates their early dropout from infertility treatments. This is because such women are unlikely to achieve successful pregnancy, and are likely to receive discouraging results early in infertility treatment. This would be especially prevalent in a highly adversely selected patient population, such as the population of the longitudinal study (see, FIG. 2). That is, a young human female with a normal number of CGG repeats on both alleles of the FMR1 gene would not be expected to benefit from treatment for infertility. A young human female with a low number of CGG repeats on at least one of the alleles of the FMR1 gene would be expected to benefit from treatment for infertility, but would be expected to abandon such treatments when they were unsuccessful.

The data from the longitudinal study supports the increased drop-out rate of infertility patients with particular FMR1 genotypes. The largest drop-out rates were seen in hom-high/high (4.3% to 0.6%), hom-low/low (3.4% to 2.8%), hom-high/low (3.9% to 1.4%) and het-norm/low (21.5% to 18.6%) FMR1 genotypes/sub-genotypes, all sub-genotypes associated with abnormally low FOR at young oocyte donor ages. By contrast, women with norm FMR1 genotypes (54.5% to 59.0%) and het-norm/high (12.5% to 17.5%) sub-genotypes increased in prevalence among fertility patients, the latter associated with comparatively good preservation of FOR into older ages (see, Gleicher V). These changes in the overall distribution of FMR1 genotypes and sub-genotypes were statistically significant (P=0.005), suggesting that women with unfavorable FOR at young ages drop out from infertility treatments earlier than women with normal FOR for their age. This also further demonstrates the importance of providing treatment for infertility and/or premature ovarian aging at young ages and before infertility is experienced. The treatment methods of the invention are therefore supported by the highly significant (P=0.005) shift in FMR1 genotype/sub-genotype distribution between young oocyte donors and older infertility patients, characterized by the relative absence in infertile women of the FMR1 genotypes associated with low FOR at young ages, strongly suggesting that such women already dropped out from infertility treatment.

A low ($CGG_{n<26}$) allele, as in a het-norm/low patient, appears to reduce pregnancy chances by approximately half in comparison to patients with the norm genotype (see, Gleicher III). All young women, however, have high FOR, which masks the reduced FOR in young women with FMR1-low genotypes. Therefore, infertility does not become clinically apparent until older age, and even detection of the differences in FOR is difficult in young women (Gleicher N., Weghofer A., Barad D. H., *Intermediate and Normal Sized CGG Repeat on the FMR1 Gene Does not Negatively Affect Donor Ovarian Response*, Human Reproduction, July 2012, 2241-2; author reply 2-3, hereinafter referred to as "Gleicher VI"; Gleicher N., Kim A., Barad D. H., et al. *FMR1-Dependent Variability of Ovarian Aging Patterns is Already Apparent in Young Oocyte Donors*, Reproductive Biology and Endocrinology, August 2013, 80, hereinafter referred to as "Gleicher VII"; and Lledo B., Guerrero J., Ortiz J. A., et al. *Intermediate and Normal Sized CGG Repeat on the FMR1 Gene Does not Negatively Affect Donor Ovarian Response*. Human Reproduction, February 2012, 609-14, hereinafter referred to as "Lledo").

The results of the longitudinal study confirm the importance of the FMR1 gene in female reproductive aging. The most important conclusion, however, is that analyzing the FMR1 gene at a young age allows a determination of risk of premature ovarian aging and infertility, and the targeted treatment of young human females. The longitudinal study demonstrates that in young human females, significant differences in AMH levels are apparent only in association with the hom-low ($CGG_{n<26}$) FMR1 genotype. Over 4 years of longitudinal follow-up, donors with the hom-high ($CGG_{n<26}$) FMR1 genotype also demonstrated significantly reduced FOR in comparison to norm donors. Single het-low donors demonstrated significantly greater ΔAMH compared to norm donors (see, FIG. 12).

FIGS. 6 and 10 show the data of longitudinal versions of earlier cross-sectional studies (see, Gleicher VI; Gleicher VII; and Lledo). FIGS. 6 and 10 show that young human females who are oocyte donors with norm and het FMR1 genotypes demonstrate similar FOR. Only young human females with the previously unexplored hom-low/low sub-genotype have significantly lower baseline FOR than young human females with the norm FMR1 genotype (FIG. 12). Only a few years later, all hom sub-genotypes (except hom-high/low), and women with even a single low ($CGG_{n<26}$) allele, are, however, adversely affected in comparison to either norm or high ($CGG_{n>34}$) allele-carrying women (see, FIGS. 12 and 13).

These findings also confirm that women with het-norm/low sub-genotypes already hyperactively recruit follicles at young ages, leading to quick depletion of FOR and early ovarian aging (see, Gleicher III). AMH is considered the best tool to assess FOR (see, Nelson II). Actively recruiting het-low women, therefore, demonstrate relatively high AMH values at young ages (FIG. 13). The two low alleles in hom-low/low females however, produce a more severely affected ovarian phenotype, characterized by significantly depleted FOR. Women with the hom-low/low genotype, have FOR loss as severe at young ages as the FOR loss seen at middle-age in women with het-low genotypes, as described in the cross sectional studies discussed in Gleicher III. Accordingly, women with the hom-low FMR1 genotype are more likely than women with het-low genotypes to experience infertility.

FIGS. 12 and 13 confirm previously noted longitudinal observations of rapid declines in AMH in het-norm/low women. Het-norm/low women experience a much larger ΔAMH than norm and het-norm/high women. Hom-low/low women decline less than het-norm/low females but start from a very low baseline at young ages. Het-norm/low females actively recruit oocytes at very young ages and apparently continue to do so into middle-age (see, Gleicher III).

The longitudinal study also indicates a difference in the ΔAMH between het-norm/low and het-norm/high, demonstrating a profound divergence in ovarian aging phenotypes after young donor ages. While het-low sub-genotypes continue to rapidly deplete FOR, het-high sub-genotypes slow their depletion. This results in unexpectedly good FOR with het-norm/high sub-genotypes at very advanced female ages (see, Gleicher V).

As previously noted, the statistical similarity in Δ AMH between het-norm/low and hom women is attributable to small patient numbers. Moreover, patients with the hom-high/low sub-genotype further distort the situation because they are evenly split between high and low FOR. It appears that FOR is determined in patients with the hom-high/low sub-genotype by which allele undergoes X chromosome-inactivation and, likely, how methylated the active X chromosome is. This sub-genotype, therefore, requires careful additional longitudinal AMH evaluations before the risk for premature ovarian aging can be determined.

The longitudinal study further found that analysis of FMR1 genotypes/sub-genotypes in young human females, as defined above, allows the detection of risk of premature ovarian aging and appropriate treatment. Women found to be at risk for premature ovarian aging based on their FMR1 genotype can be carefully followed with AMH and/or other tests of ovarian reserve, including FSH and/or androgens, recently associated with low ovarian reserve. This allows for earlier diagnosis and treatment if the tests indicate that such treatment is necessary (see, Gleicher N., Kim A., Weghofer A., et al., *Hypoandrogenism in Association with Diminished Functional Ovarian Reserve*, Human Reproduction, April 2013, 1084-91).

Finally, the longitudinal study indicated that, in a very adversely selected patient population such as the infertile women of the longitudinal study, women with disproportionally quick ovarian aging FMR1 genotypes/sub-genotypes drop out of infertility treatment early. This further demonstrates the importance of early diagnosis of premature ovarian aging to allow for timely interventions by either enhanced conception planning and/or fertility preservation by oocyte freezing or other evolving technologies. The methods of this invention allow such early detection of ovarian aging.

The longitudinal study supports the proposition that slower follicle recruitment preserves more follicles/oocytes, leading to better remaining TOR at later ages. As demonstrated by the study, low FMR1 gene alleles are associated with early depletion of OR and resulting POA/OPOI. That is, in the study, for the young oocyte donors, homozygous (hom) donors with two low alleles demonstrated significantly reduced FOR by their early 20's. Young heterozygous (het) donors with only one low allele demonstrated significantly accelerated loss of FOR in comparison with donors who only had high and/or norm alleles. By contrast, high alleles appear to preserve FOR into advanced female ages (see, Gleicher V). Analysis of FMR1 genotype in young human females, therefore, is predictive of imminent ovarian aging patterns.

In high-risk patients, the availability of age-specific normal AMH values allows for longitudinal monitoring of TOR. If patients deviate from normal AMH levels at their ages, such longitudinal monitoring allows the diagnosis of premature ovarian aging at significantly younger ages than was previously possible. The methods disclosed herein comprise: (i) identification of young human females at increased potential risk towards POA by FMR1 testing; (ii) confirmation or refutation of such risk by repeated testing of AMH (and/or other hormone parameters, such as FSH and/or androgens); and (iii) early intervention in cases where the beginning of premature ovarian aging is confirmed.

It is currently unknown what percentage of females between the ages of 16-21 would be found to be at increased risk of POA by such a screening process, and how many amongst those would develop premature ovarian aging. Considering an approximate 10% prevalence of POA in the general population, the number of patients at risk is expected to be large.

In view of the foregoing, the following methods for diagnosing imminent premature ovarian aging and infertility are described, combined with treatment and/or testing regimens that improve the possibility of potential pregnancies of human females not currently considered at risk for ovarian aging and infertility. Using FMR1 genotype data, young human females at risk for POA can be identified and treated at very young ages, when such treatment is more cost-effective and likely to be beneficial, i.e., resulting in pregnancies. Thus, the method includes routine screening of this selected "high-risk" population, determined based on FMR1 genotype analysis.

Human females with the norm-low FMR1 genotype overproduce FMRP, resulting in an increase in FMRP levels in such females as compared to human females with the norm FMR1 genotype. This increase may explain the varying reproductive success among women with the various FMR1 genotypes. Specifically, increased FMRP levels reduce reproductive success in human females with FMR1 low alleles. Therefore, administering an FMR1 inhibitor to a human female with one or more FMR1 low alleles may reduce that female's increased FMRP levels and, thereby, reduce the negative effects of her FMR1 low genotype on her reproductive success. as defined in U.S. Pat. No. 8,629,120, an FMR1 inhibitor is any compound or treatment that reduces expression of the FMR1 gene, including, without limitation, pharmaceutical agents, transcription factors, gene therapy and/or RNAi. Administering an FMR1 inhibitor may slow, arrest and/or reverse POA and/or treat infertility.

While the foregoing written description of the invention enables one of ordinary skill to make and use what is considered presently to be the best mode thereof, those of ordinary skill will understand and appreciate the existence of variations, combinations, and equivalents of the specific exemplary embodiments thereof. The invention is therefore to be limited not by the exemplary embodiments herein, but by all embodiments within the scope and spirit of the appended claims.

What is claimed is:

1. A method comprising:
   isolating an FMR1 gene from the human female;
   measuring a number of CGG repeats on each allele of the isolated FMR1 gene by using an assay;
   determining that the number of CGG repeats on at least one of the alleles of the FMR1 gene of the human female is less than 26;
   performing a testing regimen for the human female when it is determined that the number of CGG repeats on at least one of the alleles of the FMR1 gene of the human female is less than 26, said testing regimen comprising:
   periodically measuring the human female's level of a hormone related to fertility selected from the group consisting of anti-Müllerian hormone, follicle stimulating hormone, and estradiol multiple times during a period between approximately three and approximately eight years,
   after each measurement, determining if the hormone level is outside a normal range for a human female of the age of the female at the time of the measurement, and
   providing fertility treatment and/or treatment for premature ovarian aging selected from the group consisting of gene therapy, collecting and freezing eggs of the female, ovarian cryopreservation and embryo cryopreservation to the human female if it is determined that the level is outside the normal range for a human female of the age of the female at the time of the measurement; and
   wherein the method detects and treats premature ovarian aging and/or predicts infertility in a human female who has not experienced infertility and is not otherwise indicated to have ovarian aging.

2. The method of claim 1, wherein the hormone related to fertility is Anti-Müllerian Hormone, and the step of determining if the level is outside a normal range for a human female of the age of the female at the time of the measurement comprises determining if the serum level of Anti-Müllerian Hormone is less than a 95% confidence interval for a human female of the age of the female at the time of the measurement.

3. The method of claim 1, wherein the hormone related to fertility is Follicle Stimulating Hormone, and the step of determining if the level is outside a normal range for a human female of the age of the female at the time of the measurement comprises determining if the serum level of Follicle Stimulating Hormone is greater than a 95% confidence interval for a human female of the age of the female at the time of the measurement.

4. The method of claim 1, wherein the hormone related to fertility is estradiol, and the step of determining if the level is outside a normal range for a human female of the age of the female at the time of the measurement comprises determining if the serum level of estradiol is within a 95% confidence interval for a human female of the age of the female at the time of the measurement.

5. The method of claim 1, wherein the step of measuring the human female's level of a hormone related to fertility multiple times during the period between approximately three and approximately eight years is performed at approximately equal intervals over an approximately four year period.

6. The method of claim 1, wherein the step of measuring the human female's level of a hormone related to fertility multiple times during period between approximately three and approximately eight years is performed approximately annually.

7. The method of claim 1, wherein the number of CGG repeats on the alleles is determined by an assay selected from a group consisting of Southern blotting and polymerase chain reaction.

8. The method of claim 1, wherein the human female is between 21 and 28 years of age.

9. A method comprising:
   isolating an FMR1 gene from the human female;
   measuring a number of CGG repeats on each allele of the isolated FMR1 gene by using an assay;

determining an age at which the human female's biological mother entered menopause;

determining an autoimmune status of the human female;

determining that the human female is at risk of premature ovarian aging based on the number of CGG repeats on each allele of the isolated FMR1 gene, the age at which the human female's biological mother entered menopause and the autoimmune status of the human female;

performing a testing regimen for the human female when it is determined that the human female is at risk of premature ovarian aging, said testing regimen comprising:

periodically measuring the human female's level of a hormone related to fertility selected from the group consisting of anti-Müllerian hormone, follicle stimulating hormone, and estradiol multiple times during a period between approximately three and approximately eight years, after each measurement, determining if the hormone level is outside a normal range for a human female of the age of the female at the time of the measurement, and providing treatment for premature ovarian aging selected from the group consisting of gene therapy, collecting and freezing eggs of the female, ovarian cryopreservation and embryo cryopreservation to the human female if it is determined that the level is outside the normal range for a human female of the age of the female at the time of the measurement;

wherein the method detects and treats premature ovarian aging and/or predicts infertility in a human female who has not experienced infertility and is not otherwise indicated to have ovarian aging.

10. A method comprising:

isolating an FMR1 gene from the human female;

measuring a number of CGG repeats on each allele of the isolated FMR1 gene by using an assay;

determining that the number of CGG repeats on at least one of the alleles of the FMR1 gene of the human female is less than 26;

performing a first test to detect ovarian aging when it is determined that the number of CGG repeats on at least one of the alleles of the FMR1 gene of the human female is less than 26, the first test comprising at least one test of a level of a hormone related to fertility having a known range of normal values in human females at particular ages and selected from the group consisting of anti-Müllerian hormone, follicle stimulating hormone, and estradiol;

providing at least one of fertility counseling and fertility treatment to the human female when the first test shows a hormone level outside the range of normal values for a human female of the age of the human female at the time the first test was performed;

performing a plurality of second tests when the first test shows a hormone level within the normal range of values for a human female of the age of the human female at the time the first test was performed, each said second test comprising at least one test of a level of a hormone related to fertility having a known range of normal values in human females at particular ages and selected from the group consisting of anti-Müllerian hormone, follicle stimulating hormone, and estradiol, each said second test being performed at an approximate interval based in part on the hormone level shown by the first test;

providing at least one of fertility counseling and fertility treatment selected from the group consisting of gene therapy, collecting and freezing eggs of the female, ovarian cryopreservation and embryo cryopreservation to the human female when at least one of said second tests shows a hormone level outside the normal range of values for a human female of the age of the human female at the time said second test was performed; and wherein the method detects and treats premature ovarian aging and/or predicts infertility in a human female who has not experienced infertility and is not otherwise indicated to have ovarian aging.

11. The method of claim 10, further comprising performing a plurality of third tests when a last performed second test shows a hormone level within the normal range of values for a human female of the age of the human female at the time the test was performed, each said third test comprising at least one test of a level of a hormone related to fertility having a known range of normal values in human females at particular ages and selected from the group consisting of anti-Müllerian hormone, follicle stimulating hormone, and estradiol, each said third test being performed at an approximate interval based in part on the hormone level shown by a last performed second test; and providing at least one of fertility counseling and fertility treatment selected from the group consisting of gene therapy, collecting and freezing eggs of the female, ovarian cryopreservation and embryo cryopreservation to the human female when at least one of said third tests shows a hormone level outside the normal range of values for a human female of the age of the human female at said time the third test was performed.

12. The method of claim 10, wherein the interval at which the second tests are performed is approximately annually when the first test shows a hormone level within the normal range of values for a human female of the age of the human female at the time the first test was performed.

13. The method of claim 10, wherein the interval at which the second tests are performed is approximately annually and the second tests are performed within a period of approximately three to approximately five years, when the first test shows a hormone level within the normal range of values for a human female of the age of the human female at the time the first test was performed, and thereafter performing a plurality of third tests when a last performed second test shows a hormone level within the normal range of values for a human female of the age of the human female at the time said last performed second test was performed, each said third test comprising at least one test of a level of a hormone related to fertility having a known range of normal values in human females at particular ages and selected from the group consisting of anti-Müllerian hormone, follicle stimulating hormone, and estradiol, each said third test being performed at an interval of approximately two years during a period of approximately five to approximately eight years.

14. The method of claim 10, wherein the approximate interval at which the second tests are performed is between three and twelve months when the first test shows a hormone level within the normal range of values for a human female of the age of the human female and outside a 68% confidence interval of the mean level for a human female of the age of the human female at the time the first test was performed.

15. The method of claim 10, wherein the human female is from 21 to 28 years of age.

* * * * *